United States Patent [19]
Landoll

[11] Patent Number: 5,667,864
[45] Date of Patent: Sep. 16, 1997

[54] ABSORBANT LAMINATES AND METHOD OF MAKING SAME

[76] Inventor: Leo M. Landoll, 1 Ice Pond Trail, Hockessin, Del. 19707

[21] Appl. No.: 487,754

[22] Filed: Jun. 7, 1995

[51] Int. Cl.$^6$ .................................................. B32B 1/04
[52] U.S. Cl. .................. 428/74; 156/251; 156/290; 156/308.2; 156/308.4; 156/309.9; 428/76; 428/138; 604/366; 604/370; 604/378; 604/383; 604/385.1; 442/361; 442/398
[58] Field of Search ......................... 156/251, 290, 156/308.2, 308.4, 309.9; 428/74, 76, 138, 286, 296, 302; 604/366, 370, 378, 383, 385.1

[56] References Cited

U.S. PATENT DOCUMENTS

| | | |
|---|---|---|
| 3,285,245 | 11/1966 | Eldredge . |
| 3,846,205 | 11/1974 | Yazawa . |
| 4,041,203 | 8/1977 | Brock . |
| 4,214,582 | 7/1980 | Patel . |
| 4,348,445 | 9/1982 | Craig . |
| 4,545,372 | 10/1985 | Lauritzen . |
| 4,657,802 | 4/1987 | Morman . |
| 4,726,976 | 2/1988 | Karami . |
| 4,883,707 | 11/1989 | Newkirk . |
| 5,114,787 | 5/1992 | Chaplin . |
| 5,246,772 | 9/1993 | Manning . |
| 5,362,546 | 11/1994 | Boulanger . |

*Primary Examiner*—James C. Cannon
*Attorney, Agent, or Firm*—Caesar, Rivise, Bernstein, Cohen & Pokotilow, Ltd.

[57] ABSTRACT

Absorbent laminates include an oriented, fluid-pervious plastic substrate bonded to a nonwoven absorbent member. The nonwoven absorbent member includes bi-component fibers having a heat-softenable outer skin, said heat-softenable outer skin being heat-softenable at a temperature lower than the melting point and shrinking point of the oriented plastic substrate to provide a binder component for the laminate. A fluid-pervious plastic substrate can be adhered to one or both surfaces of the nonwoven absorbent member through bi-component fibers of the nonwoven absorbent member. In absorbent laminates including opposed fluid-pervious outer plastic substrates marginal edges of the laminate can be compression sealed through the bi-component fibers in the intermediate nonwoven absorbent member to seal the edges against the escape of fibers from the laminate. Methods of forming absorbent laminates of this invention also form a part of the present invention.

39 Claims, 3 Drawing Sheets

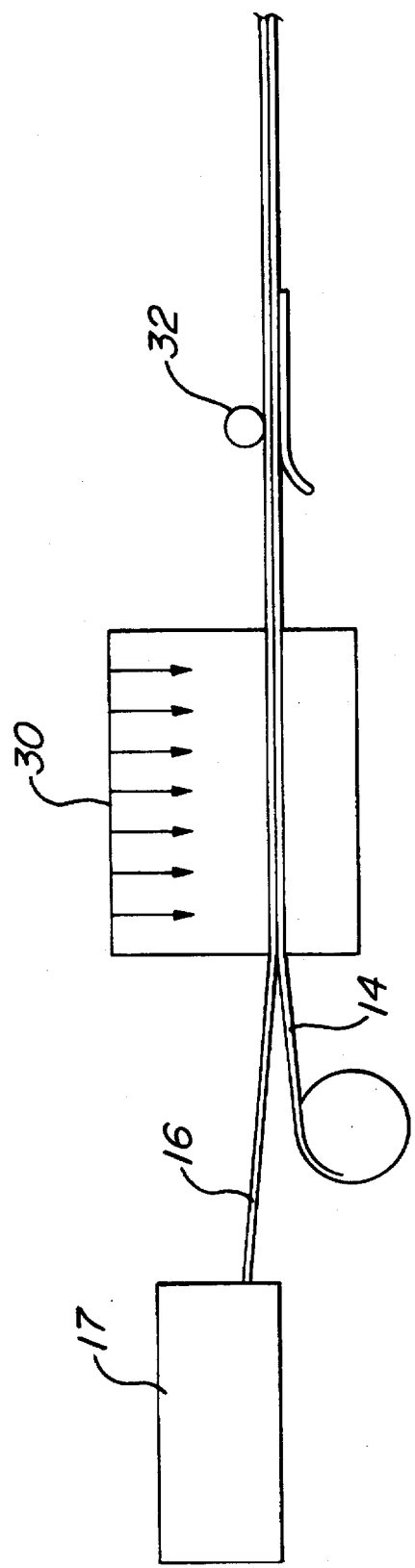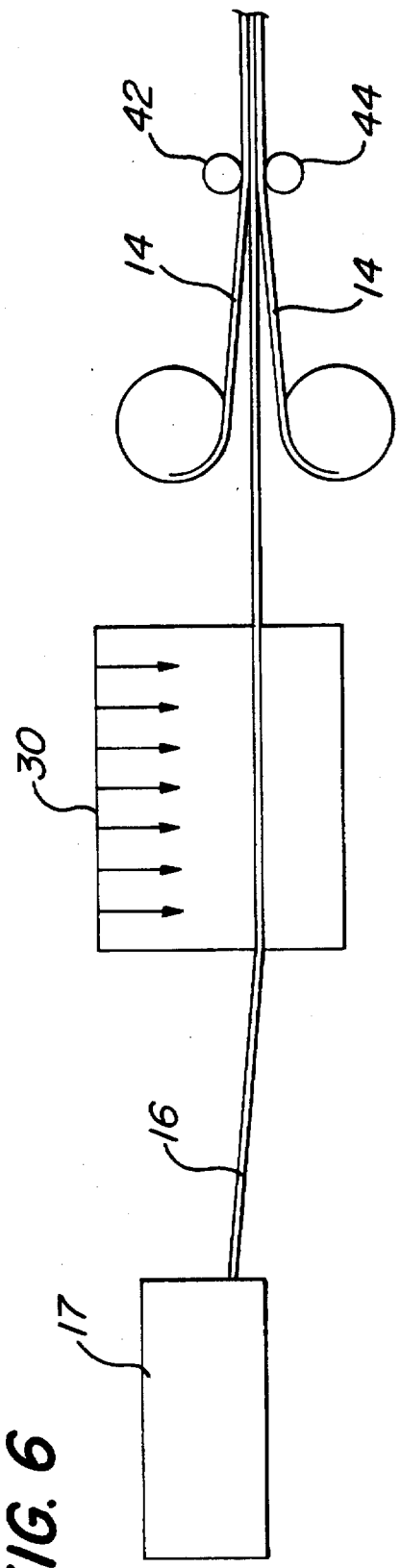

ABSORBANT LAMINATES AND METHOD OF MAKING SAME

FIELD OF THE INVENTION

This invention relates generally to absorbent laminates and to methods of making same. In accordance with a preferred form of the invention the laminate is an absorbent non-stick pad employed as the absorbent component in an adhesive bandage or in a non-stick wound dressing.

BACKGROUND ART

Absorbent non-stick pads employed as the absorbent components in high quality adhesive bandages preferably include an oriented apertured web laminated to a nonwoven absorbent material. In one prior art structure the oriented apertured web is a high density polyethylene web sold under the trademark DELNET by Applied Extrusion Technologies, Inc. of Peabody, Mass. 01960, and the nonwoven absorbent material is a needle-punched web including a blend of polypropylene and rayon fibers. In this prior art structure the DELNET web has anti-stick properties relative to body wounds to be covered, and the nonwoven absorbent material has a weight of approximately 3.8 oz./yd$^2$. These two components are heat sealed together in a bonding nip under high pressure to insure that the components are effectively bonded together and to constrain the oriented aperture web against shrinking under the temperature conditions required to effect the bonding operation.

While the above described prior art structure has functioned in a satisfactory manor in bandage applications, that structure is undesirably expensive to fabricate, particularly because of the relatively high cost of the needle-punched nonwoven absorbent component of the pad. Moreover, the high pressure required at the bonding nip to effect bonding of the nonwoven absorbent component to the oriented aperture web, while controlling, or preventing, shrinkage of the oriented web, results in the formation of an absorbent pad that has an excessively high fiber density and little entrapped air. This undesirably limits the absorbent capacity of the pad. Moreover, the required use of a high bonding pressure makes the prior art process somewhat difficult to control.

Prior art pads of the type described above generally have a thickness of 40 mils, and when incorporated into a bandage by compression generally have a thickness of approximately 35 mils., with the overall thickness of the bandage being 50 mils.

It also should be noted that nonwoven single and multi-layer constructions employing bi-component filaments and/or fibers have been disclosed in the prior art, as evidenced by U.S. Pat. No. 5,382,400 (Pike et al.); U.S. Pat. No. 5,082,720 (Hayes); U.S. Pat. No. 4,883,707 (Newkirk) U.S. Pat. No. 5,246,772 (Manning) U.S. Pat. No. 4,732,809 (Harris, Jr. et al.). However, none of these prior art patents discloses or suggests the formation of laminated constructions including a fluid-pervious, oriented plastic substrate bonded to a nonwoven absorbent web including bi-component fibers in it, as in the present invention.

The Pike et al. '400 patent discloses the formation of single and multi-layer nonwoven webs employing helically crimped bi-component filaments. The disclosed bi-component filaments can include a polypropylene core surrounded by a polyethylene sheath. In the disclosed multi-layer constructions each layer includes bi-component filaments in it, with the degree of crimp of the bi-component filaments in one layer being different from the degree of crimp of the bi-component filaments in the other layer. (column 10, line 36 et. seq.).

The Hayes '720 patent discloses melt-bondable, bi-component fibers and nonwoven webs made from such fibers. The bi-component fibers include a core having an at least partially crystalline polymer and a sheath including a compatible blend of polymers including at least one amorphous polymer and at least one partially crystalline polymer. The polymer sheath melts at a temperature lower than that of the polymer core.

The Newkirk '707 patent discloses a laminate of two carded webs having bi-component fibers in them. Bonding of the fibers in each web and between the webs is achieved by thru-air bonding with heated air to thereby activate the sheath layer of the bi-component fibers. The laminated carded web is described for use as coverstock for disposable diapers, sanitary napkins, and the like.

The Manning '772 patent discloses a laminate including an airlaid, nonwoven pulp web layer on opposed sides of, and reinforced by a wetlaid bi-component web layer. The bi-component web layer includes bi-component fibers wherein the sheath component has a lower melting point than the core component. Bonding of the layers is effected through the sheath of the bi-component fibers, and also preferably by utilizing an additional latex adhesive.

The Harris Jr. et al. '809 patent discloses the use of bi-component filaments or staple fibers in forming nonwoven webs. The disclosure is directed to a bi-component filament including a polyester core and another latently adhesive component (e.g., the sheath) having a melting point below that of the core.

The prior art also discloses other multi-layer constructions intended to obviate the problem of shrinkage during the bonding of the various layers to each other. For example, note U.S. Pat. No. 4,348,445, to Craig, wherein a laminate is disclosed that includes an unoriented film formed of a propylene/1-butene copolymer bonded to a netting layer including oriented fibers. This patent discloses laminates wherein two of such film layers are bonded to a central netting layer, and wherein two netting layers are bonded to a central film layer. The selection of materials allegedly prevents shrinkage or distortion of the oriented netting layer(s) during the bonding of the multiple layers into a laminate construction.

The prior art also includes numerous additional disclosures of multi-layer and/or multi-fiber fabrics wherein one or more of the fibers/layers is a thermoplastic material that functions as a bonding agent in the fabric. For example, note the disclosures in U.S. Pat. No. 5,362,546 (Boulanger); U.S. Pat. No. 4,545,372 (Lauritzen) U.S. Pat. No. 4,041,203 (Brock et al.) U.S. Pat. No. 3,846,205 (Yazawa); U.S. Pat. No. 4,657,802 (Morman); U.S. Pat. No. 4,726,976 (Karami et al.); U.S. Pat. No. 4,214,582 (Patel); U.S. Pat. No. 3,285,245 (Eldredge et al.) and U.S. Pat. No. 5,114,787 (Chapline et al.). However, none of these latter patents discloses or suggests the formation of laminated constructions including a fluid-pervious, oriented plastic substrate bonded to a nonwoven absorbent web including bi-component fibers in it, as in the present invention.

The Boulanger '546 patent discloses a nonwoven fabric intended for use as a facing layer on a molded fibrous mat. The nonwoven fabric is a laminated structure including a first layer having bond-forming fibers (e.g., low melt polyester, polyethylene and polyamide) mixed with and bonded to filler fibers (e.g., rayon, acrylic, cotton, polyester and polypropylene fibers) and a second layer including fibers (e.g., high melting point polyester fibers) that will not melt at the fusion temperature of the bond-forming fibers of the first layer. These two layers are intermingled together in a process that forms the nonwoven fabric into the general configuration shown in FIG. 5 of the '546 patent.

The Lauritzen '372 patent discloses an adhesive bandage construction employing a nonwoven fabric including a mixture of absorbent fibers (e.g., rayon staple fibers, cotton fibers, short length natural cellulose fibers such as wood pulp fibers and cotton linters, and mixtures thereof) and conjugate fibers (e.g., bi-component fibers including a polyester core and a polyethylene sheath). In one embodiment a light weight veneer of heat-fusible fibers is provided on each surface of the nonwoven fabric and will bond to each other and to the adjacent nonwoven fabric at the temperatures employed to activate the bonding properties of the conjugate fibers of the nonwoven fabric.

The Brock et al. '203 patent discloses a nonwoven fabric laminate including a top layer in the form of a mat including thermoplastic microfibers and a bottom layer in the form of a web of substantially continuous and randomly deposited, molecularly oriented filaments. These layers can be secured to each other by the application of heat and pressure at intermittent areas along the fabric, or alternatively by using an independently applied adhesive or by the mechanical interlocking of the fibers, such as be needling techniques well know in the art.

The Yazawa '205 patent discloses a flexible, gas-permeable nonwoven material including a web of split fibers secured with a shaped binder (e.g., a perforated film) that preferably is of the same polymer as the split fiber but that has a lower melting point than the split fiber by virtue of being unoriented.

The Mormon '802 patent discloses a nonwoven elastic substrate including an elastic web (e.g., melt blown fibrous nonwoven elastic web or aperture web of an elastic film) that is heat bonded to a fibrous nonwoven gatherable web while the elastic web is maintained in a stretched condition. Thereafter the stretching or biasing force is removed from the composite nonwoven elastic substrate, resulting in the nonwoven elastic web returning to its unstretched, relaxed condition with the nonwoven gatherable web being gathered.

The Karami et al. '976 patent discloses a composite substrate usable as a coversheet on disposable articles such as disposable diapers, sanitary napkins, disposable bed pads, nursing pads, finger dressings and incontinent diapers, or the like. The substrate includes a thermoplastic film secured to and between fibrous webs through a heat embossing operation that also forms apertures in the thermoplastic film.

The Patel '582 patent discloses a multi-layer surgical dressing employing a multi-layer nonwoven fabric including outer surface layers employing heat-sensitive fibers such as polypropylene, nylon, or textile-length polyester fibers, and an interior layer employing polyester binder fibers that soften at a temperature lower than the fibers in the outer surface layers. This patent also discloses the bonding of a gauze fabric to the nonwoven fabric by melting heat sensitive fibers adjacent the gauze fabric.

The Eldredge et al. '245 patent discloses an absorbent wound dressing including a multi-layer pad formed in a continuous process, wherein the non-stick top, or release, layer of polypropylene fibers is heated to melt the fibers and aid in securing the top layer to the underlying absorbent fibers (e.g., cellulose acetate fibers).

The Chaplin et al. '787 patent discloses a multi-layer nonwoven web including at least one layer of a self-bonded fibrous nonwoven web bonded to at least one layer of a carded web. As disclosed the fibrous nonwoven web can include thermoplastic filaments comprising a variety of different polymers, e.g., polypropylene, high density polyethylene, low density polyethylene, linear low density polyethylene, polyamides, polyester, blends of polypropylene and linear low density polyethylene. The carded web can include a variety of staple fibers, e.g., cotton, polypropylene, blends of polypropylene and polybutenes and blends of polypropylene and linear low density polyethylene.

The disclosures of all of the patents identified in this Background Art section are incorporated herein by reference.

Based on the state of the prior art applicant has determined that the need exists for an absorbent, non-stick laminate that is less expensive to fabricate than prior art structures, that can be easily fabricated without the use of excessively high pressures required in prior art processes to effect bonding and to control shrinkage, and that has improved absorbent properties. It is to such a construction that the present invention is directed.

OBJECTS OF THE INVENTION

It is a general object of this invention to provide absorbent laminates that overcome the deficiencies of prior art absorbent structures.

It also is a general object of this invention to provide processes for producing absorbent laminates that overcome the deficiencies of prior art processes.

It is a specific object of this invention to provide absorbent laminates that are economical to construct.

It is a specific object of this invention to provide absorbent laminates having improved absorbent properties.

It is specific object of this invention to provide absorbent laminates and processes for making such laminates that eliminate, or reduce, excessive shrinkage in an oriented plastic substrate (e.g., an oriented aperture web) of the laminates.

It is a specific object of this invention to provide a simplified, continuous process for forming absorbent laminates in accordance with this invention.

SUMMARY OF THE INVENTION

These and other objects of the instant invention are achieved by providing an absorbent laminate comprising a fluid-permeable (preferably liquid-permeable), oriented (uniaxial or biaxial) plastic substrate (preferably aperture) bonded to a nonwoven absorbent member, said nonwoven absorbent member including bi-component fibers having a heat-softenable outer skin, said heat-softenable outer skin being heat softenable at a temperature lower than the melting point and shrinking point of the oriented plastic substrate to produce a binder component for the laminate.

In one embodiment of the invention the heat-softenable outer skin bonds the fibers of the nonwoven absorbent member together and also bonds the nonwoven absorbent member to the oriented plastic substrate.

In a further embodiment of the invention the oriented plastic substrate is a multi-layer, laminated oriented plastic film or net (preferably formed by coextrusion) wherein the layer of the coextruded substrate contiguous to the nonwoven absorbent member is a low melt temperature, heat-softenable skin that is heat-softenable at a temperature lower than the heat-softening temperature of the outer skin employed in bi-component fibers forming part of the nonwoven absorbent member, said low melting skin of the multi-layer oriented plastic substrate providing a bonded connection between the substrate and the nonwoven absorbent member.

In the preferred embodiment of this invention the absorbent member of the laminate is a dry-formed member including bi-component fibers intermingled with other fibers.

In a preferred embodiment of the invention the absorbent member of the laminate is a dry-formed member including bi-component fibers therein, said dry-formed member being formed by a fiber entanglement process (e.g., needle punching) to provide a laminate construction having a high Z-axis strength.

In the preferred embodiment of this invention the outer skin of the bi-component fibers of the absorbent member is a polyolefin and the other fibers of the absorbent member also are polyolefin fibers. Preferably the oriented plastic substrate also is a polyolefin substrate, and most preferably a polyethylene substrate.

In accordance with this invention the absorbent laminate can include three (3) or more layers having at least one layer in the form of a fluid-permeable, oriented plastic substrate and at least one layer of a nonwoven absorbent member including bi-component fibers therein having a skin melting temperature below the melting point or shrinkage point of the oriented plastic substrate(s) in the composite laminate construction.

In one preferred embodiment of this invention a composite lamination includes outer layers in the form of fluid permeable, oriented plastic substrates and a nonwoven absorbent member including bi-component fibers therein disposed between the outer layers. The bi-component fibers in the intermediate layer have a skin softening temperature below the melting point and shrinking point of the oriented plastic substrates.

In a further preferred form of this invention a multicomponent lamination including outer, oriented plastic substrates and an interior nonwoven absorbent member including bi-component fibers therein is in the form of a dressing for wounds, and optionally can include medicaments or other wound treating ingredients therein.

In a preferred embodiment of this invention a multicomponent lamination includes outer, fluid-permeable, oriented plastic substrates and a nonwoven absorbent member including bi-component fibers therein disposed between both substrates, with edges of the lamination being compression heat-sealed through heat activation of the heat-softenable outer skin of the bi-component fibers of the nonwoven absorbent member, without adversely affecting the higher loft properties of the nonwoven absorbent member intermediate the bonded edges.

In a further form of the invention a composite laminate includes a fluid-permeable, oriented plastic substrate on one side thereof, a fluid-impermeable substrate on the opposite side thereof, and an intermediate absorbent layer including at least one bi-component fiber therein having a skin with a melting point lower than the melting point and shrinking point of the two outer layers. The layers of the laminate can be easily bonded together without adversely affecting the high loft absorbent properties of the product by activating the heat-softenable skin of the bi-component fibers. Thereafter, the laminate can be cut and bonded selectively along the edges to fuse together the laminate at the edges by a rotary die-cutting or hot die-stamping operation to provide, in an economical and uncomplicated process, completed articles with sealed edges (e.g., panty shields, feminine napkins and the like).

In a method of forming an absorbent laminate comprising an oriented, fluid-pervious plastic substrate bonded to a nonwoven absorbent member, said nonwoven absorbent member including bi-component fibers having a heat-softenable outer skin thereon, said method including the steps of forming an array of fibers including said bi-component fibers therein, heating the array of fibers to a temperature for softening the outer skin of the bi-component fibers to a sufficient degree for bonding said array of fibers together to form said nonwoven absorbent member and for bonding said nonwoven absorbent member to the oriented plastic substrate, wherein said temperature for bonding the fibers together and for bonding the absorbent member to the oriented plastic substrate is below the temperature at which the oriented plastic substrate shrinks or otherwise becomes distorted, positioning said array of fibers contiguous to the plastic substrate, and applying pressure to said array of fibers and plastic substrate after said array of fibers has been heated to said sufficient degree to thereby bond the array of fibers together into said nonwoven absorbent member and to bond the nonwoven absorbent member to the plastic substrate.

In accordance with one method of this invention the step of heating the array of fibers takes place after the array of fibers is positioned contiguous to the plastic substrate.

In accordance with another method of this invention the step of heating the array of fibers takes place before the array of fibers is positioned contiguous to the plastic substrate.

In accordance with one aspect of this invention, the array of fibers is formed as a multi-layer construction by positioning a thin layer comprising predominantly bi-component fibers in overlying relationship with one or more additional layers comprising a lower percentage of bi-component fibers than in said thin layer, said thin layer being disposed contiguous to the oriented plastic substrate to thereby bond the nonwoven material to said substrate through bi-component fibers of said thin layer. Most preferably the thin layer is formed solely of bi-component fibers, and the additional layers of fibers include from about 20% bi-component fibers to less than 100% bi-component fibers.

In accordance with another method of forming an absorbent laminate comprising a pair of oriented, fluid-pervious plastic substrates, said substrates being bonded to opposed surfaces of a nonwoven absorbent member, said nonwoven absorbent member including bi-component fibers having a heat-softenable outer skin thereon, said method including the steps of forming an array of fibers including said bi-component fibers therein, heating the array of fibers to a temperature for softening the outer skin of the bi-component fibers to a sufficient degree for bonding said array of fibers together to form said nonwoven absorbent member and for bonding said nonwoven absorbent member to each one of the pair oriented plastic substrates, wherein said temperature for bonding the fibers together and for bonding the absorbent member to the pair of oriented plastic substrates is below the temperature at which the oriented plastic substrates shrinks or otherwise becomes distorted, positioning said array of fibers contiguous to and between the pair of plastic substrates, and applying pressure to said array of fibers and plastic substrates after said array of fibers has been heated to said sufficient degree to thereby bond the array of fibers together into said nonwoven absorbent member and to bond the nonwoven absorbent member to the plastic substrates.

BRIEF DESCRIPTION OF THE DRAWINGS

The above and other objects and many attendant features of this invention will become readily appreciated as the same becomes better understood by reference to the following detailed description when considered in connection with the accompanying drawings wherein:

FIG. 5 is a schematic view of a part of a continuous process in accordance with this invention for forming the absorbent member illustrated in FIGS. 1 and 2;

FIG. 6 is a schematic view of a part of a second continuous process in accordance with this invention for forming the absorbent member illustrated in FIGS. 3 and 4;

DESCRIPTION OF THE PREFERRED EMBODIMENTS OF THE INVENTION

Figure 1:
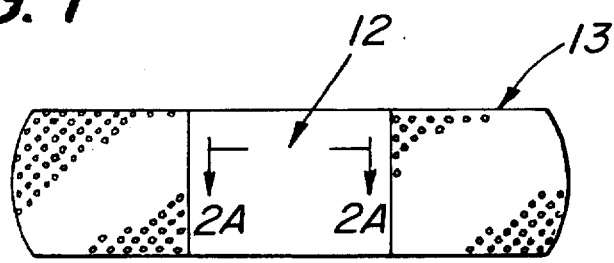
FIG. 1 is a plan view of a bandage employing a laminated absorbent member in accordance with this invention.

Referring now in greater detail to the various figures of the drawing wherein like reference characters refer to like parts, an adhesive bandage 10 employing a unique absorbent laminate 12 in accordance with the present invention is shown generally in FIG. 1.

Figure 2B:
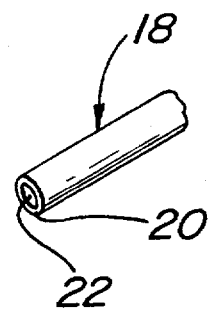
FIG. 2B is an enlarged, fragmentary isometric view showing the general construction of a bi-component fiber employed in the present invention
Figure 2A:
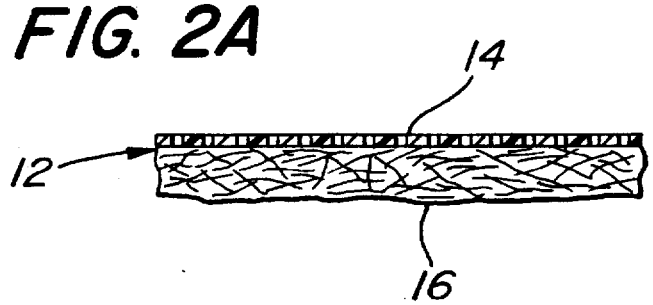
FIG. 2A is an enlarged sectional view taken along line 2A—2A of FIG. 1.

Referring to FIG. 2A, the absorbent laminate 12 in accordance with one aspect of this invention includes an oriented, plastic web or substrate 14 bonded to a nonwoven absorbent member 16. The nonwoven absorbent member 16 includes bi-component fibers 18 therein (see FIG. 2B). These bi-component fibers have an outer skin or sheath 20 for use in heat bonding the fibers of the nonwoven absorbent member 16 together and for heat bonding the nonwoven absorbent member 16 to the plastic web 14, wherein the temperature for bonding the fibers together in the absorbent member 16 and for bending the absorbent member 16 to the plastic web 14 is below the temperature at which the oriented plastic web will melt, shrink or distort.

In a preferred embodiment of this invention the oriented plastic web or substrate 14 is apertured to permit fluids to pass therethrough into the underlying nonwoven absorbent member 16. Most preferably the oriented plastic web 14 is an oriented polyethylene web and the bi-component fiber 18 includes an outer skin 20 of a substantially unoriented polyethylene, wherein the melting or bonding temperature of the unoriented polyethylene skin of the bi-component fiber is lower than the temperature at which the oriented polyethylene web 14 will melt or shrink. Thus the temperature required to soften the polyethylene skin of the bi-component fiber to permit the skin to function as a binder in the laminate (i.e., approximately 116°–123° C.) is lower than the temperature that softens the oriented polyethylene web 14 to a degree that causes the oriented web to shrink or otherwise distort (i.e., approximately 127° C.). Therefore the oriented web 14 will not melt, shrink or otherwise become undesirably distorted during the bonding operation, i.e., during the step of heating the structure 12 to a temperature at which the skin or sheath 20 of the bi-component fiber 18 becomes sufficiently tacky to function as a binder to secure together the fibers in the nonwoven web 16 as well as to secure the nonwoven web 16 to the oriented web 14.

Most preferably the oriented aperture web or substrate 14 employed in this invention is sold under the trademark DELNET by Applied Extrusion Technologies, Inc. having its corporate offices at 3 Centennial Drive, Peabody, Mass. 01960. Such aperture webs, including an identification of various polymers usable in the webs and an identification of methods employed to form such webs are disclosed in U.S. Pat. Nos. 4,842,794 and 5,207,962, both being assigned to Applied Extrusion Technologies, Inc. and covering inventions made jointly by Edward E. Hovis and Eric D. Johnson. The subject matter of these latter applications is hereby incorporated by reference.

Referring to FIG. 2B, the bi-component fiber 18 employed in this invention preferably has a polypropylene core 22 and a polyethylene skin or sheath 20, and is sold under the brand name Herculon 425 by Hercules, Inc., having corporate offices located in Wilmington Del. In the fabrication of this fiber the polypropylene core 22 sets up and crystallizes at a temperature (i.e., approximately 125° C.) at which the polyethylene skin 20 is still molten, and therefore the orienting stress is taken up completely by the polypropylene core, which is the carrier for the polyethylene skin, and the polyethylene skin remains unoriented.

It should be understood that this invention is not limited to the use of the specific bi-component fiber 18 described above. However, the bi-component fiber 18 that is employed in this invention needs to have an outer skin that can be brought to a softening temperature sufficient to permit the softened skin to bond the bi-component fibers together with any other fibers employed in the nonwoven material 16 and also to bond the nonwoven material 16 to the oriented plastic web 14 without causing the oriented plastic web to melt or excessively distort.

In accordance with a preferred form of the invention the nonwoven absorbent member 16 is a carded web comprising approximately 70% polypropylene fibers (e.g., Herculon 196) and approximately 30% of the bi-component fiber 18 (e.g., Herculon 425).

Forming the nonwoven absorbent material 16 with a dry-formed mix of polypropylene fibers and bi-component fibers 18 including a polyethylene skin 20 disposed about a polypropylene core 22 is a preferred construction because polypropylene is relatively inexpensive and also bonds best to other polyolefins, such a polyethylene.

In accordance with this invention applicant has made a laminated pad or member 12 having a thickness of approximately 53 mils. with approximately 2 oz. of fibers in the nonwoven web 16 and with an absorption of approximately 17 grams of water per gram of pad.

In distinction to this invention, a prior art pad as described earlier in this application (i.e., one having a DELNET aperture web and a needle-punched blend of polypropylene fibers and rayon fibers) has a thickness of approximately 40 mils with approximately 3.8 oz of fibers in the needle-punched blend and an absorption of approximately 7 grams of water per gram of pad.

It is known that for a given weight of fibers a pad having greater loft or thickness will have the greatest absorbency. It also is know that absorbency can be increased by increasing the weight of fibers present in the pad. However, this latter-mentioned approach for increasing absorbency increases the cost of fabricating the pad by increasing the cost of materials utilized in the pad.

A very desirable feature of the present invention is that a pre-consolidated absorbent material, such as the prior art needle-punched web, need not be employed. Rather, the laminated web can be made in a single, continuous in-line process in accordance with this invention, as is described hereinafter.

Although a desirable feature of the present invention is that it is not necessary to employ a pre-consolidated absorbent material, such as a needle-punch web, as the nonwoven absorbent component of the laminated construction, for some applications it may be desirable to employ a highly entangled fiber assemblage as the nonwoven absorbent component 16, such as an assemblage formed by needle-punching or other fiber entanglement process. However, even in accordance with this form of the invention the nonwoven absorbent member 16 includes bi-component fibers 18 therein. The use of a highly entangled fiber assemblage as the nonwoven absorbent component 16 provides a structure having a higher Z-axis, or Z-direction, strength than other laminates of this invention wherein the nonwoven absorbent member 16 is not formed by any fiber entanglement process (e.g., needle-punching).

Although the nonwoven absorbent component 16 of the laminate 12 could be made from 100% bi-component fibers 18, such a construction would be unnecessarily expensive. Most preferably, the nonwoven web 16 includes approximately 30% by weight of bi-component fibers 18 and approximately 70% by weight of polypropylene fibers. It is believed that a lesser weight percent of bi-component fibers 18 could possibly be used, but that percentages of 15% or less would result in a product that would not have the requisite stability to function in a pad 12 of the bandage 10, at least when the nonwoven absorbent material 16 is not a highly entangled fiber assemblage, such as a needle-punched assemblage. However, when the nonwoven absorbent member 16 is either needle-punched or formed by another type of fiber-entanglement process that materially increases the Z-direction strength of the assemblage, the percentage of bi-component fibers 18 employed in the web may be materially reduced, and can be relied upon principally to bond the nonwoven absorbent member 16 to the oriented web 14. In other words, when the integrity of the nonwoven absorbent member 16 is enhanced by a fiber entanglement process it may not be necessary to rely upon the bi-component fibers 18 to tightly bond the fibers of the nonwoven assembly together to establish a structurally stable laminate.

Referring to FIG. 5, in accordance with one method of this invention a carded nonwoven absorbent material 16 as described above is formed in a carding machine, which is schematically indicated at 17, and is laid onto an oriented DELNET web 14 upstream of a thru-air heating oven 30 in which the heated air is directed downwardly, as is schematically indicated by the arrows, so as to cause the heated air to pass through the nonwoven absorbent material 16 prior to reaching the DELNET web 14. The heating step is carried out at a temperature to soften the skin or sheath 20 of the bi-component fibers 18 sufficiently to permit the skin or sheath to function as a binder for the other fibers in the absorbent web 16 and also as a binder for securing the absorbent web 16 to the underlying DELNET web 14. After the laminate leaves the oven 30 it is subjected to a low pressure consolidating step, which may be carried out with an unheated roll 32.

Figure 3:
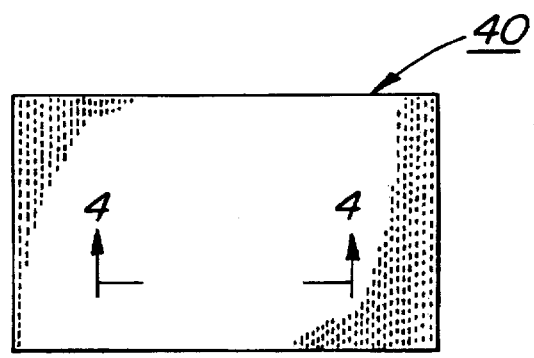
FIG. 3 is a plan view of a sterile bandage in accordance with a second embodiment of this invention
Figure 4:
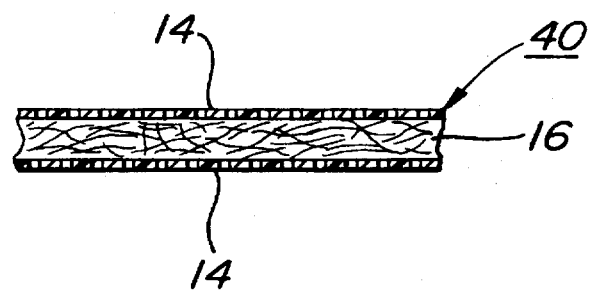
FIG. 4 is an enlarged sectional view of the sterile bandage taken along line 4—4 of FIG. 3.

Referring to FIGS. 3 and 4, it also is within the scope of this invention to provide a three-component laminated construction in the form of a sterile bandage 40. Both outer surfaces of the bandage 40 are non-stick surfaces, and therefore, either side of the bandage can be placed adjacent an injured skin area of a person.

The nonwoven absorbent material 16 in the bandage 40 is sandwiched between oriented plastic webs 14, such as the oriented DELNET webs described earlier herein. However, in fabricating the three-component construction 40 it has been determined that the outer oriented plastic webs 14, whether aperture or not, should not be combined with the absorbent nonwoven web 16 upstream of the thru-air heating oven 30. If the plastic webs 14 are combined with the nonwoven web 16 prior to entering the heating oven, the top plastic web, by virtue of being the first component engaged by the downwardly directed stream of hot air, tends to shrink and distort at the temperatures required to soften the outer skin 20 of the bi-component fibers 18 of the nonwoven inner layer 16 to a degree that is sufficient to both bend together the fibers of the inner layer 16 and also to bond the inner layer 16 to the outer plastic web 14.

To deal with the above discovered problem in forming a three-component laminate, the outer plastic webs 14 are laminated to the nonwoven fabric 16 after the nonwoven fabric has been directed through the hot air oven 30. (See FIG. 6). The lamination operation most likely will be carried out with heated metal rolls 42, 44 forming a nip therebetween, with the heat being controlled so that the outer oriented plastic webs 14 are not heated to a heat-distorting/shrinking temperature.

In accordance with the broadest aspects of this invention it is not required that the marginal edges of the sterile bandage 40 be compressed into a seal region for the purposes of fully enclosing high loft regions of the nonwoven absorbent material 16. However, if desired, or for applications where it is necessary, the marginal edges of multi-component laminates in accordance with this invention, including the sterile bandage 40, can be sealed in a unique manner in accordance with this invention, as will be described hereinafter in connection with the embodiments illustrated in FIGS. 9 and 11.

Figure 7:
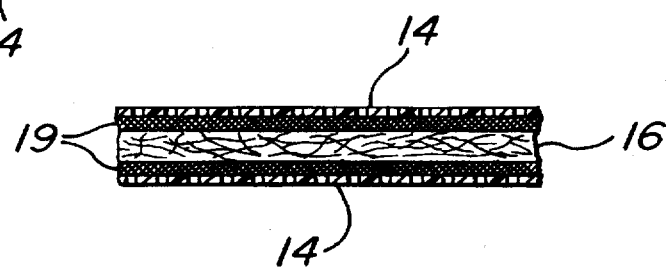
FIG. 7 is a sectional view similar to FIG. 4, but showing still another embodiment of a laminated construction in accordance with this invention.

Referring to FIG. 7, if it is necessary or desirable to enhance bonding to the oriented plastic substrate(s) 14 the nonwoven member 16 can include thin layer(s) 19 of 100% bi-component fibers on one or both surfaces thereof to provide a high concentration of bonding material (i.e., the sheath 20 of the bi-component fibers 18) for adhering to the contiguous plastic substrate(s) 14, e.g., either one plastic substrate in the adhesive bandage 10 or opposed plastic substrates of the sterile bandage 40 as described earlier herein.

In the embodiment illustrated in FIG. 7 the laminate includes opposed oriented plastic substrates 14 on each side of the nonwoven member 16, and therefore a pair of thin layers 19 are included on each surface of the nonwoven member 16.

Figure 8:
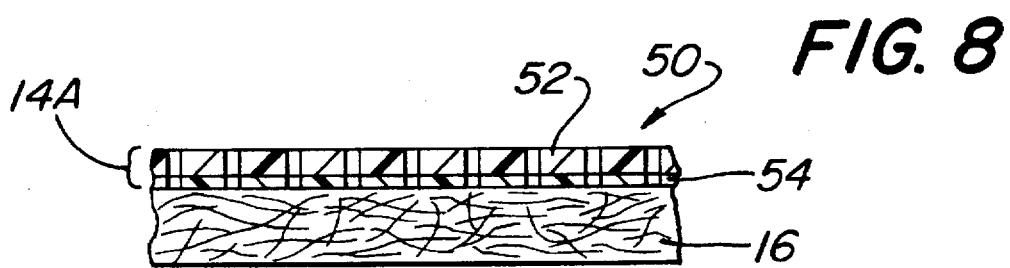
FIG. 8 is a sectional view showing still another embodiment of a laminated construction in accordance with this invention.

Referring now to FIG. 8, a further embodiment of this invention in the form of a laminate construction 50 is illustrated. The laminate 50 differs from the laminate 12 by employing a multi-layer (52,54), fluid-pervious, oriented plastic web or substrate 14A, preferably formed by a coextrusion process. The outer layer 52 of the web 14A can be of the same construction and made of the same polymers as the plastic web or substrate 14 employed in the previously-described embodiments of this invention. The inner layer 54 preferably is thinner than the outer layer constitutes a low melting skin that functions as the principal bonding component for adhering the web 14A to the nonwoven absorbent member 16.

Still referring to FIG. 8, as in the earlier described embodiments of this invention the nonwoven absorbent member 16 is a fiber assemblage including bi-component fibers 18 therein. However, unlike the previously described embodiments of this invention the melting temperature of the skin 54 of the multilayer oriented plastic web 14A is lower than the heat-softening temperature of the outer skin or sheath 20 of the bi-component fibers 18. Thus, in the laminate 50 the low melting point skin 54 of the oriented plastic web 14A is the principal component relied upon for bonding the oriented plastic web 14A to the underlying nonwoven absorbent member Referring to FIG. 9, still a further embodiment of an absorbent laminate in accordance with this invention is illustrated at 60. The laminate 60 is in the form of a wound dressing having opposed facing sheets in the form of fluid pervious, plastic webs or substrates 14 therein. These substrates 14 can be of the same construction as described in connection with previous embodiments of this invention.

Figure 9:
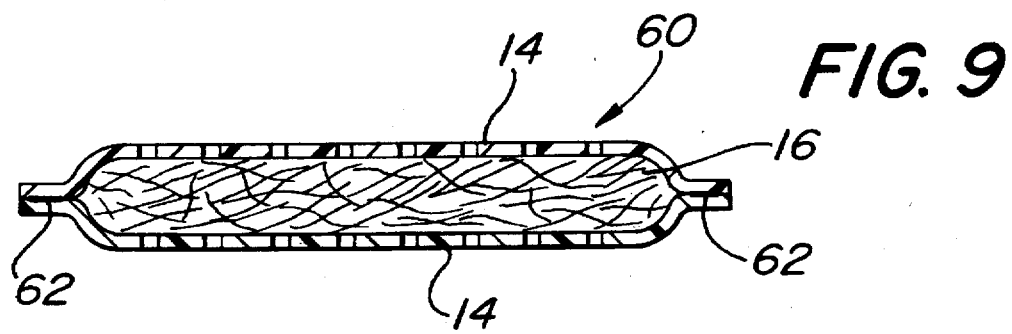
FIG. 9 is a sectional view showing still another embodiment of a laminated construction in accordance with this invention.

Still referring to FIG. 9, the laminate 60 includes a nonwoven absorbent member 16 including bi-component fibers 18 therein. The construction of this nonwoven absorbent member 16 can be the same as described in connection with the previously disclosed embodiments of this invention.

The significant distinction between the wound dressing 60 illustrated in FIG. 9 and the previous embodiments of the invention described herein is with respect to the construction of peripheral edges 62. Specifically the peripheral edges of the dressing 60 are sealed through the outer skin or sheath 20 of the bi-component fibers forming part of the assemblage of the nonwoven absorbent member 16. This is accomplished by applying heat and pressure to the edges.

It should be noted that prior art constructions employing bi-component fibers 18 therein generally have employed such fibers for the purpose of maintaining, or establishing, high loft in the bonded construction. Applicant, on the other hand, has found that by appropriate control of the bonding operation the high loft construction of the nonwoven absorbent member 16 can be maintained in the central region of the absorbent component of the dressing 60, while the marginal edges of the pad 60 can be compression-heat bonded to melt the outer sheath 20 of the bi-component fibers and thereby provide a continuous sealed perimeter that prevents fibers of the interior assemblage 16 from escaping from within the confines of the outer plastic substrates 14.

In an exemplary embodiment of the invention illustrated in FIG. 9, a laminate 60 including a nonwoven absorbent member 16 having a weight of 2.5 oz./yd.$^2$ maintains a high loft construction in the central region thereof with the edges of the substrates 14 being thin, compression bonded regions 62 that are bonded together through the bi-component fibers 18 of the nonwoven member 16. This construction is achieved by first passing the composite laminate construction at a speed in the range of 15–20 feet per minute through a bonding nip formed by metal rolls heated to approximately 123° C. and maintained at 50 psi. At this speed the fiber assemblage 16 maintains high loft while having the fibers thereof bonded together through the bi-component fibers 18, and with the bi-component fibers also bonding the assemblage 16 to the oriented plastic webs 14.

However, at a substantially slower processing speed, e.g., on the order of 1 foot/minute, through the nip of the heated (e.g., approximately 123° C.) metal bonding rolls, the outer sheath 20 of the bi-component fibers 18 actually fuse into a continuous mass that bonds the edges of the opposed substrates 14 into a tight, compressed seal region 62 through which fibers of the nonwoven absorbent member 16 cannot escape. This arrangement in which fiber escapage from the interior of the laminate is prevented is extremely important for certain applications, and in particular for wound dressings which are required to be bacteria/virus proof.

Thus, in the embodiment illustrated in FIG. 9 the opposed substrates 14 are bonded over substantially their entire area to the nonwoven absorbent member 16, both in the high loft central region and in the sealed margins 62 thereof.

Figure 10:
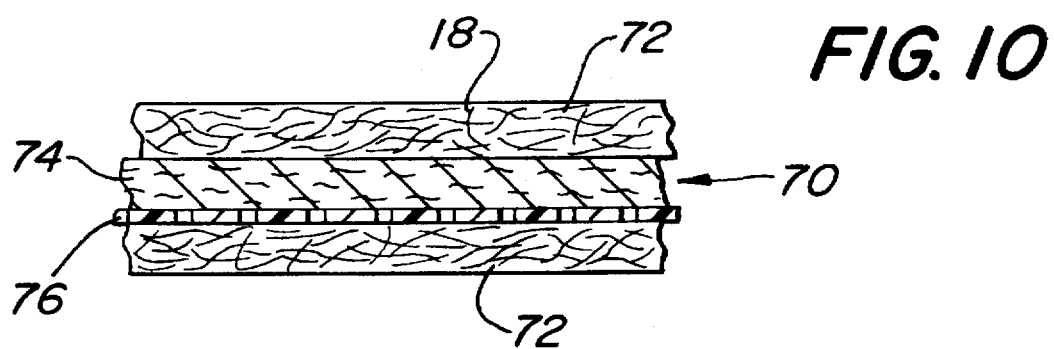
FIG. 10 is a sectional view showing still a further embodiment of a laminated construction in accordance with this invention.

Referring now to FIG. 10, a further embodiment of a composite laminate in accordance with this invention is illustrated at 70. Composite laminates in accordance with this aspect of the invention can include alternating and/or contiguous layers comprising fiber assemblages having bi-component fibers therein. These bi-component fibers include a skin that melts at a temperature below the melting point and shrink point of oriented plastic web(s) within the composite laminate construction.

Still referring to FIG. 10, an exemplary multilayer laminate 70 includes four layers. The opposed outer layers 72 are dry formed nonwoven fabrics employing polypropylene fibers and bi-component fibers 18 therein. In the illustrated embodiment of this invention the bi-component fibers 18 include a outer skin of a substantially unoriented polyethylene surrounding an oriented core of oriented polypropylene.

An internal layer 74 adjacent one of the outer layers 72 is in the form of a cotton fiber layer employing a suitable bonding fiber in the construction, (e.g., a fusible polyester fiber). An additional layer 76 located between the layer 74 and the other outer layer 72 is in the form of a microporous polyolefin film. It should be noted that in this construction three of the four layers employ low melting bi-component or fusible fibers therein so that these fibers can be employed to bond all of the layers of the laminate together without the need to use additional thermal or pressure activated adhesives therein.

It should be understood that the multi-component laminate 70 in FIG. 10 is for illustrative purposes only, it being understood that the particular construction and/or make up of each of the layers of the laminate is selected on the basis of the specific needs or intended uses of the product. However, in accordance with this invention at least one of the layers of the laminate includes bi-component fibers of the type illustrated at 18 in FIG. 2B, and at least one layer of a fluid pervious, oriented plastic substrate.

Figure 11:
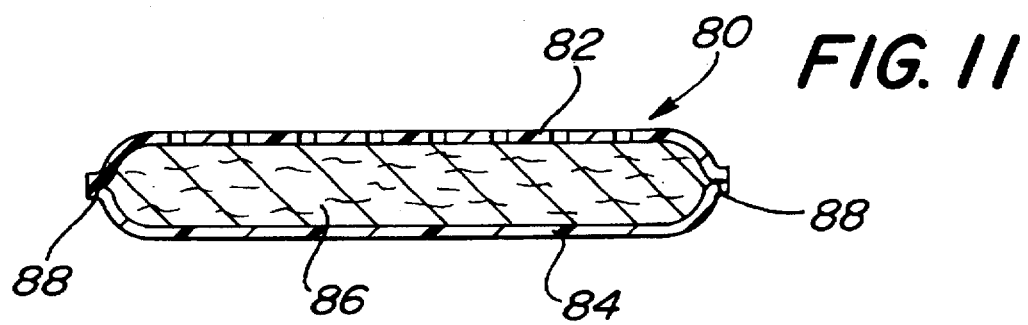
FIG. 11 is a sectional view showing still another embodiment of a laminated construction in accordance with this invention.

Referring to FIG. 11 yet a further embodiment of this invention is illustrated at 80. The laminate 80 is in the form of a panty shield or feminine napkin including an outer, fluid-pervious, soft facing sheet or web 82, a fluid-impervious backing sheet or web 84, and a middle absorbent layer 86. The facing sheet or web 82 preferably is in the form of a fluid pervious, oriented plastic substrate, such as the DELNET product described earlier in this application.

The middle or intermediate absorbent layer 86 can be a fiber assemblage including bi-component fibers 18 therein, as described earlier in this application, and the fluid-impervious web 84 can be in form of an extruded polyethylene sheet, as is well known in the disposable diaper and/or sanitary napkin art.

As can be seen in FIG. 11, the absorbent laminate 80, like the absorbent laminate 60 illustrated in FIG. 9, includes a high loft central region and thin, compressed bonded peripheral edge regions 88. This arrangement of a high loft central region and compressed edge regions 88 is achieved by the same bonding operation described earlier herein with respect to the formation of the laminate 60 illustrated in FIG. 9.

The particular nonwoven web 16 employed in this invention can be formed in a variety of ways, and can include a number of different constructions. For example, although in a preferred form of the invention the nonwoven web 16 is formed by a carding operation, it also is within the scope of this invention to form the nonwoven web by an airlay process or other process for forming nonwoven fabrics. As stated earlier, it also is within the scope of this invention to employ a nonwoven absorbent member 16 in the form of a highly entangled fiber assemblage provided by a needle-punch process or other fiber entanglement process.

Moreover, the nonwoven web 16 can be a single layer construction including bi-component fibers 18 in it, preferably ranging from 20% to 100% of the fiber composition of the web, or the web can include multiple layers that differ from each other in the fiber composition. For example, the nonwoven web 16 can include one or two outer layers having a higher concentration of bi-component fibers 18 therein than one or more interior layers. As an example, and not intended as limiting the present invention, the nonwoven web 16 can include one or two thin out layers including 100% bi-component fibers 18 (depending upon whether the nonwoven web 16 is required to be heat bonded through the skin 20 of the bi-component fibers 18 to either one or two out layers of an oriented plastic substrate 14) and one or more other layers including different percentages of bi-component fibers 18 in them. However, it is preferred that each layer of the nonwoven web 16 have at least about 20% bi-component fibers 18 therein, by weight, to assure adequate bonding together of all of the fibers in each of the layers, and the bonding of each of the layers to its adjacent layer.

It should be understood that all references to the percentage of fibers refers to the percentage of fibers, by weight.

It also should be understood that reference to the various components of the laminate being of a specific polymer, e.g., "polypropylene" fibers, "polyethylene" web 14, "polyethylene" sheath 20 and "polypropylene" core 22 of the bi-component fiber 18, does not preclude the inclusion of other ingredients/polymers therein, provided that over fifty percent (50%) by weight of the fibers is formed of the referenced polymer.

Without further elaboration, the foregoing will so fully illustrate my invention that others may, by applying current or future knowledge, adopt the same for use under various conditions of service.

What is claimed as the invention is:

1. An absorbent laminate comprising an oriented, fluid-pervious plastic substrate having a melting point and a shrinking point, said plastic substrate being bonded to a nonwoven absorbent member, said nonwoven absorbent member including bi-component fibers having a heat-softenable outer skin, said heat-softenable outer skin being heat-softenable at a temperature lower than the melting point and the shrinking point of the oriented plastic substrate to provide a binder component for the laminate.

2. The absorbent laminate of claim 1, wherein said nonwoven absorbent member is a dry-formed member including said bi-component fibers intermingled with other fibers.

3. The absorbent laminate of claim 2, wherein the outer skin of the bi-component fibers is a polyolefin and said other fibers are polyolefin fibers.

4. The absorbent laminate of claim 1, wherein said oriented plastic substrate is permeable to liquid.

5. The absorbent laminate of claim 1, wherein said oriented plastic substrate is an apertured web.

6. The absorbent laminate of claim 1, wherein said oriented plastic substrate is a polyolefin substrate.

7. The absorbent laminate of claim 6, wherein the outer skin of the bi-component fibers is a polyolefin.

8. The absorbent laminate of claim 6, wherein said nonwoven absorbent member includes said bi-component fibers intermingled with other fibers.

9. The absorbent laminate of claim 8, wherein the outer skin of the bi-component fibers is a polyolefin and said other fibers are polyolefin fibers.

10. The absorbent laminate of claim 6, wherein said polyolefin substrate is pervious to liquid.

11. The absorbent laminate of claim 6, wherein said polyolefin substrate comprises polyethylene.

12. The absorbent laminate of claim 6, wherein said polyolefin substrate is an apertured substrate comprising polyethylene.

13. The absorbent laminate of claim 12, wherein the outer skin of the bi-component fibers is a polyolefin.

14. The absorbent laminate of claim 12, wherein said nonwoven absorbent member includes said bi-component fibers intermingled with other fibers.

15. The absorbent laminate of claim 14, wherein the outer skin of the bi-component fibers is a polyolefin and said other fibers are polyolefin fibers.

16. A method of forming an absorbent laminate comprising an oriented, fluid pervious plastic substrate bonded to a nonwoven absorbent member, said nonwoven absorbent member including bi-component fibers having a heat-softenable outer skin thereon, said method including the steps of:

forming an array of fibers including said bi-component fibers therein, heating the array of fibers to a temperature for softening the outer skin of the bi-component fibers to a sufficient degree for bonding said array of fibers together to form said nonwoven absorbent member and for bonding said nonwoven absorbent member to the oriented plastic substrate, wherein said temperature for bonding the fibers together and for bonding the absorbent member to the oriented plastic substrate is below the temperature at which the oriented plastic substrate will shrink or otherwise become distorted, positioning said array of fibers contiguous to the plastic substrate, and applying pressure to said array of fibers and plastic substrate after said array of fibers has been heated to said sufficient degree to thereby bond the array of fibers together into said nonwoven absorbent member and to bond the nonwoven absorbent member to the plastic substrate.

17. The method of claim 16, wherein the step of heating the array of fibers takes place after said positioning step.

18. The method of claim 16, wherein the step of heating the array of fibers takes place before said positioning step.

19. The method of claim 16, wherein the array of fibers is formed by mixing together said bi-component fibers and other fibers.

20. The method of claim 19, wherein said bi-component fibers include an outer skin comprising a polyolefin and said other fibers comprise polyolefin fibers.

21. The method of claim 16, wherein said array of fibers is formed as a multi-layer construction by positioning a thin layer comprising predominantly bi-component fibers in overlying relationship with one or more additional layers comprising a lower percentage of bi-component fibers than in said thin layer, said thin layer being disposed contiguous to the oriented plastic substrate to thereby bond the nonwoven material to said substrate through bi-component fibers of said thin layer.

22. The method of claim 21 wherein said thin layer is formed solely of bi-component fibers.

23. The method of claim 21, wherein said additional layers of fibers include from about 20% bi-component fibers to about 100% bi-component fibers.

24. A method of forming an absorbent laminate comprising a pair of oriented plastic substrates, at least one of said plastic substrates being fluid pervious, said substrates being bonded to opposed surfaces of a nonwoven absorbent member, said nonwoven absorbent member including bi-component fibers having a heat-softenable outer skin thereon, said method including the steps of:

forming an array of fibers including said bi-component fibers therein, heating the array of fibers to a temperature for softening the outer skin of the bi-component fibers to a sufficient degree for bonding said array of fibers together to form said nonwoven absorbent member and for bonding said nonwoven absorbent member to each one of the pair oriented plastic substrates, wherein said temperature for bonding the fibers together and for bonding the absorbent member to the pair of oriented plastic substrates is below the temperature at which the oriented plastic substrates will shrink or otherwise become distorted, positioning said array of fibers contiguous to an between the pair of plastic substrates, and applying pressure to said array of fibers and plastic substrates after said array of fibers has been heated to said sufficient degree to thereby bond the array of fibers together into said nonwoven absorbent member and to bond the nonwoven absorbent member to the plastic substrates.

25. The method of claim 24, wherein the step of heating the array of fibers takes place after said positioning step.

26. The method of claim 24, wherein the step of heating the array of fibers takes place before said positioning step.

27. The method of claim 24, wherein the array of fibers is formed by mixing together said bi-component fibers and other fibers.

28. The method of claim 27, wherein said bi-component fibers include an outer skin comprising a polyolefin and said other fibers comprise polyolefin fibers.

29. The method of claim 24, wherein said array of fibers is formed as a multi-layer construction by positioning outer thin layers comprising predominantly bi-component fibers in overlying relationship with one or more additional inner layers comprising a lower percentage of bi-component fibers than is in said thin outer layers.

30. The method of claim 29, wherein said thin outer layers are formed solely of bi-component fibers.

31. The method of claim 29, wherein said additional inner layers of fibers include from about 20% bi-component fibers to about 100% bi-component fibers.

32. The absorbent laminate of claim 1, wherein said bi-component fibers bond fibers of the nonwoven absorbent member together and bond the nonwoven absorbent member to the oriented plastic substrate.

33. The absorbent laminate of claim 1, wherein said nonwoven absorbent member is a needle-punched absorbent member.

34. The absorbent laminate of claim 1, wherein said nonwoven absorbent member includes a higher concentration, by weight, of bi-component fibers contiguous to the plastic substrate than in the interior of said nonwoven absorbent member.

35. An absorbent laminate comprising a multi-layer substrate bonded to a nonwoven absorbent member, one of said layers of said substrate being an oriented, fluid-pervious plastic film and the other of said layers being a low melt skin for bonding said multilayer substrate to said nonwoven absorbent member, said nonwoven absorbent member including bi-component fibers having a core and heat-softenable outer skin, said heat-softenable outer skin of said bi-component fibers having a melting point and softening point lower than the melting point and softening point of the core of the bi-component fibers and higher than the melting point and softening point of the low melting skin of the multilayer substrate, both said low melt skin of the substrate and the heat-softenable outer skin of the bi-component fibers comprising a binder for the absorbent laminate.

36. An absorbent laminate comprising outer oriented, fluid-pervious plastic substrates and an intermediate nonwoven absorbent member disposed between and bonded to said outer substrates, said nonwoven absorbent member including bi-component fibers having a heat-softenable outer skin bonding fibers of the nonwoven absorbent member together and bonding the nonwoven absorbent member to the oriented plastic substrates.

37. The absorbent laminate of claim 36 wherein said nonwoven absorbent member includes a higher concentration, by weight, of bi-component fibers at the surfaces of the nonwoven absorbent member contiguous to the oriented, fluid-pervious plastic substrates then in the interior of said nonwoven absorbent member.

38. An absorbent laminate comprising a facing layer adapted to be positioned against a person's skin, a backing layer adapted to be positioned remote from the skin, and a nonwoven absorbent member disposed between the facing layer and the backing layer, said facing layer being an oriented, fluid-pervious plastic substrate bonded to said nonwoven absorbent member, said backing layer being a liquid-impermeable substrate bonded to said nonwoven absorbent member, said nonwoven absorbent member including bi-component fibers having a heat-softenable outer skin for bonding said nonwoven absorbent member to both said facing layer and said backing layer.

39. The absorbent laminate of claim 38 including peripheral regions of said facing layer and said backing layer being secured together in compressed, sealed margins through bi-component fibers of the nonwoven absorbent member, said sealed margins providing a sealed barrier for preventing fibers of the nonwoven absorbent member from escaping from the laminate marginal areas.

* * * * *